United States Patent [19]

McSpadden

[11] Patent Number: 5,735,689
[45] Date of Patent: Apr. 7, 1998

[54] ENDODONTIC DENTAL INSTRUMENT

[75] Inventor: John T. McSpadden, Chattanooga, Tenn.

[73] Assignee: Tycom Dental Corporation, Irvine, Calif.

[21] Appl. No.: 570,642

[22] Filed: Dec. 11, 1995

[51] Int. Cl.$^6$ .................................................. A61C 5/02
[52] U.S. Cl. ............................................................. 433/102
[58] Field of Search ............................................. 433/102

[56] References Cited

U.S. PATENT DOCUMENTS

| | | | |
|---|---|---|---|
| 1,022,838 | 4/1912 | Funk | 433/102 |
| 1,067,015 | 7/1913 | Fowler | 433/102 |
| 1,211,537 | 1/1917 | Burton . | |
| 1,307,446 | 6/1919 | Kerr | 433/102 |
| 2,035,298 | 3/1936 | Caldwell | 145/117 |
| 2,084,737 | 6/1937 | Magnus | 77/72 |
| 2,328,629 | 9/1943 | Eich et al. | 145/117 |
| 2,769,355 | 11/1956 | Crisp | 77/70 |
| 2,966,081 | 12/1960 | Kallio | 77/70 |
| 3,443,459 | 5/1969 | Mackey et al. | 77/70 |
| 3,947,143 | 3/1976 | Gulla | 408/230 |
| 3,971,135 | 7/1976 | Leu | 32/48 |
| 3,991,454 | 11/1976 | Wale | 29/105 |
| 4,209,275 | 6/1980 | Kim | 408/211 |
| 4,330,229 | 5/1982 | Croydon | 408/212 |
| 4,332,561 | 6/1982 | McSpadden | 433/102 |
| 4,457,710 | 7/1984 | McSpadden | 433/81 |
| 4,536,159 | 8/1985 | Roane | 433/224 |
| 4,538,989 | 9/1985 | Apairo et al. | 433/102 |
| 4,602,900 | 7/1986 | Arpaio et al. | 408/230 |
| 4,661,061 | 4/1987 | Martin | 433/102 |
| 4,758,156 | 7/1988 | Johnson | 433/81 |
| 4,871,312 | 10/1989 | Heath | 433/102 |
| 4,894,011 | 1/1990 | Johnson | 433/81 |
| 4,904,185 | 2/1990 | McSpadden | 433/164 |
| 4,934,934 | 6/1990 | Arpaio et al. | 433/102 |
| 5,035,617 | 7/1991 | McSpadden | 433/102 |
| 5,035,618 | 7/1991 | Katz | 433/102 |
| 5,088,863 | 2/1992 | Imanaga | 408/230 |
| 5,104,316 | 4/1992 | McSpadden | 433/102 |
| 5,106,298 | 4/1992 | Heath et al. | 433/102 |
| 5,219,284 | 6/1993 | Velvarte | 433/102 |
| 5,387,059 | 2/1995 | Borzemsky | 408/226 |
| 5,464,362 | 11/1995 | Heath et al. | 451/48 |

FOREIGN PATENT DOCUMENTS

| | | |
|---|---|---|
| 775.073 | 12/1934 | France . |
| 279144 | 10/1913 | Germany . |
| 949002 | 3/1956 | Germany . |
| 623 224 A5 | 5/1981 | Switzerland . |
| 622 588 | 9/1978 | U.S.S.R. . |
| 715 238 | 2/1980 | U.S.S.R. . |
| 1419624 | 12/1975 | United Kingdom . |
| 2 035 806 A | 6/1980 | United Kingdom . |
| 2035806 | 6/1980 | United Kingdom . |

OTHER PUBLICATIONS

Metal Cutting Tool Handbook Published by: Metal Cutting Tool Institute, Jul. 1965.

Der Wirkungsmechanismus der Wurzelkanal–Erweiterer Author: J. Walter, Budapest (4 pages) (including English translation: The Effective Mechanism of Root Canal Reamers By: J. Walter, Budapest (10 pages) From The Clinic of Preservative Dentistry, Semmelweis Medical University, Budapest, Hungary (1971).

Primary Examiner—John J. Wilson
Attorney, Agent, or Firm—Knobbe, Martens, Olson & Bear, LLP

[57] ABSTRACT

The present invention is directed to improved endodontic dental instruments for extirpating and enlarging a root canal and methods for use thereof. The dental instruments of the invention include a helical radial land and a helical blade edge spaced from the land on its opposite sides by helical flutes. Dental instruments according to the invention exhibit improved and more balanced side cutting in curvilinear canals and non-circular canal areas such as fins or anastomosis canal regions.

18 Claims, 5 Drawing Sheets

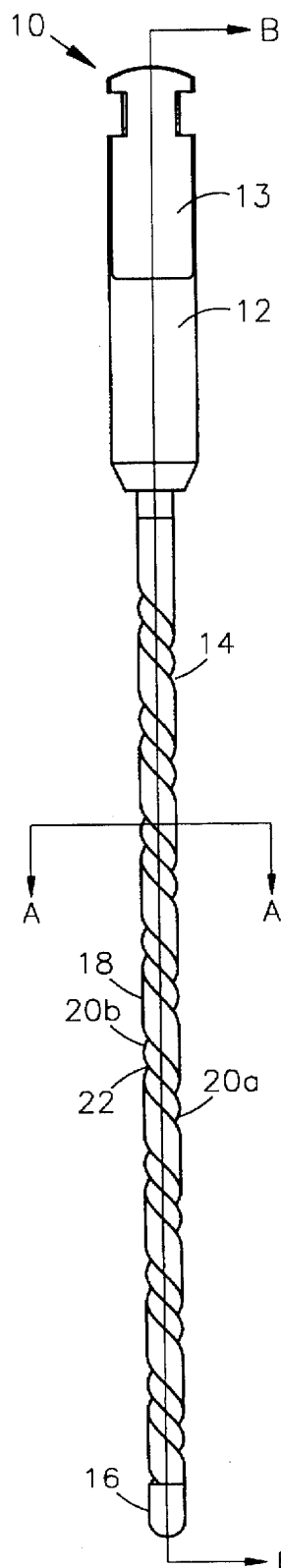
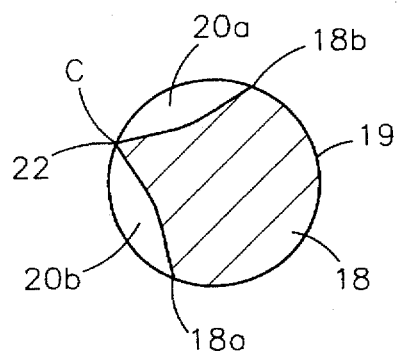
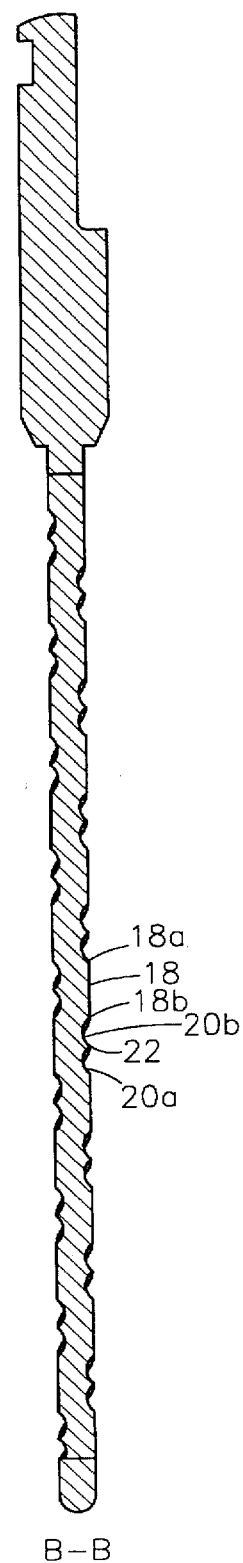
Fig. 1
Fig. 2
Fig. 3

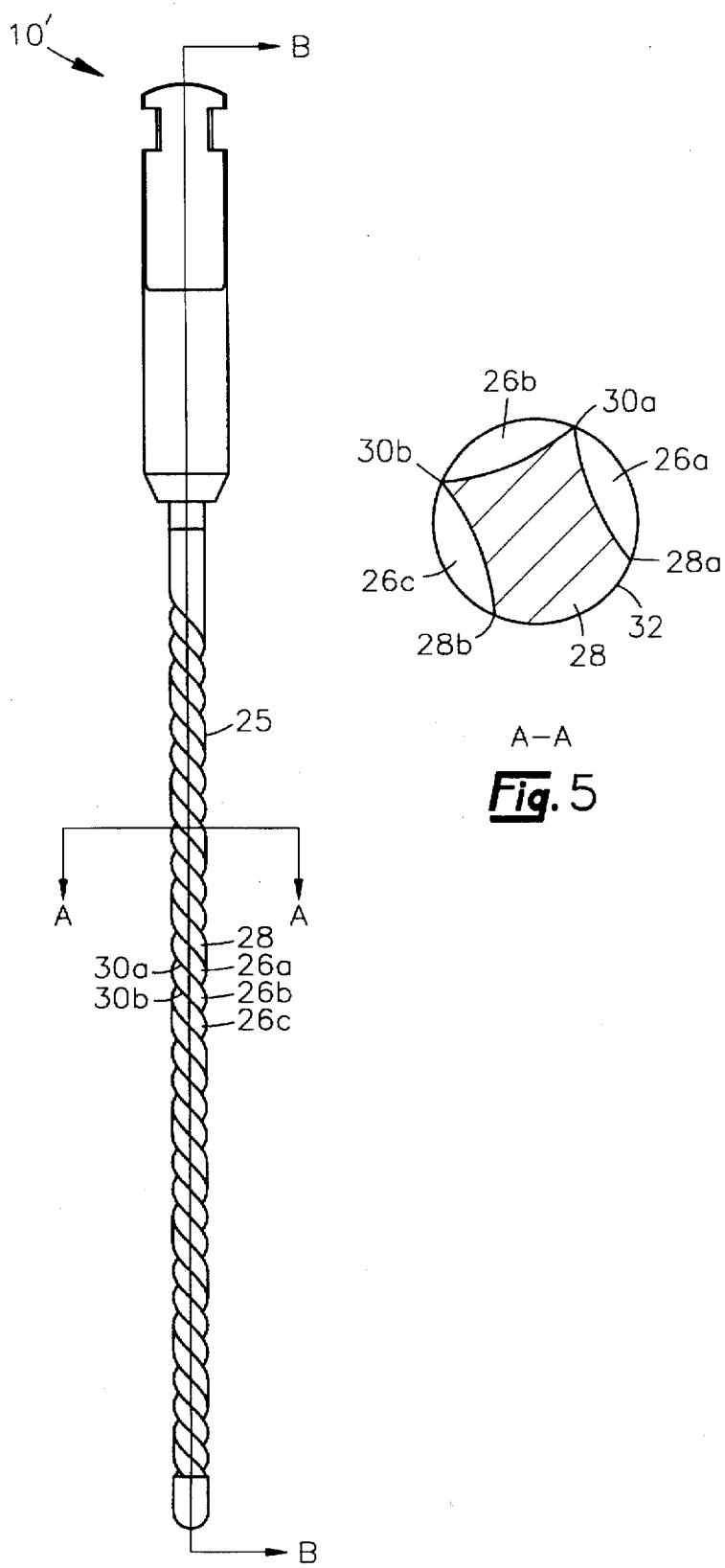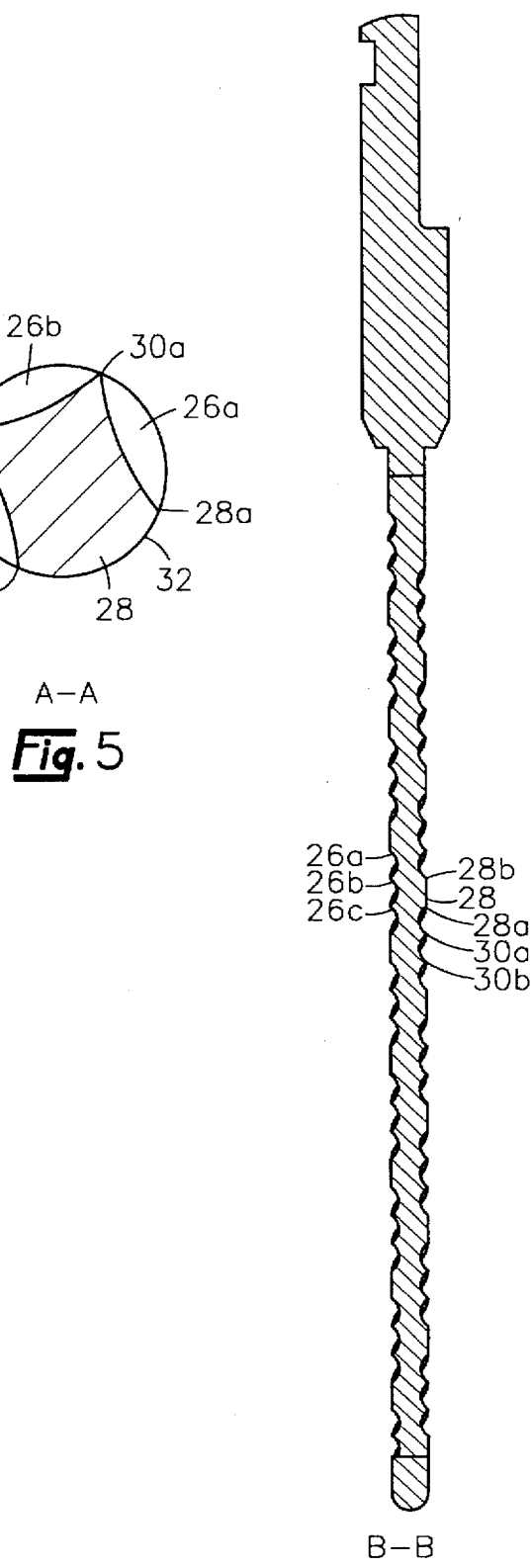
Fig. 4  Fig. 5  Fig. 6

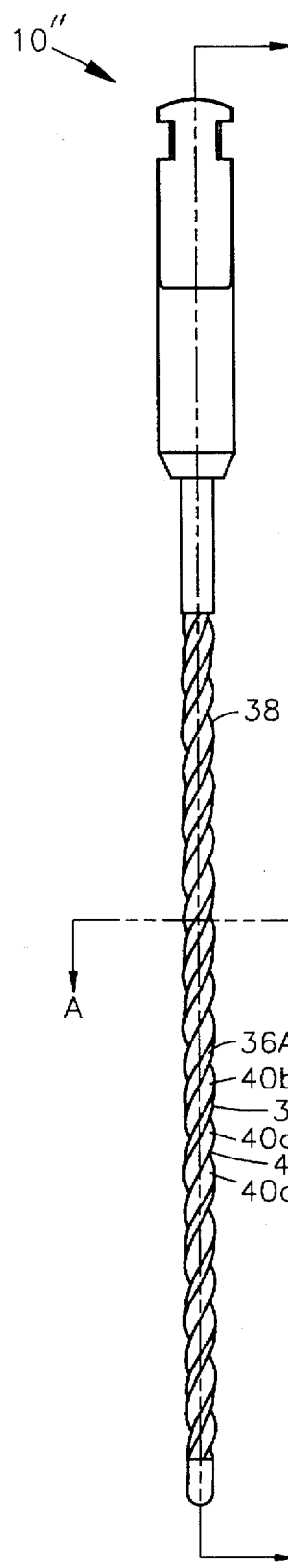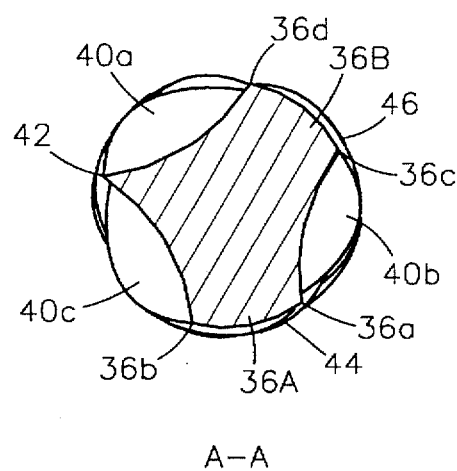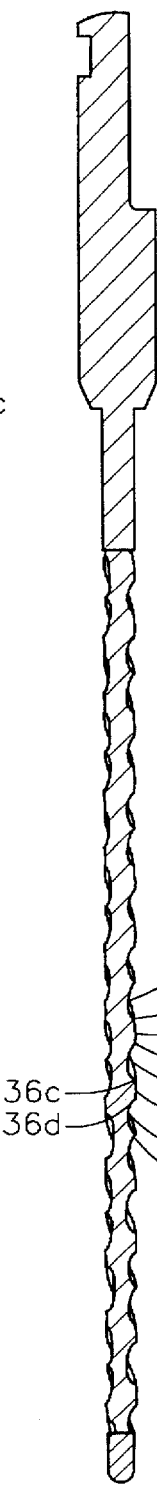
Fig. 7
Fig. 8
Fig. 9

A-A

B-B

A-A

B-B

ENDODONTIC DENTAL INSTRUMENT

FIELD OF INVENTION

The invention relates generally to the field of endodontics and more particularly to instruments and methods for extirpating and enlarging a root canal.

BACKGROUND OF THE INVENTION

In the field of endodontics, one of the most important and delicate procedures is that of cleaning or extirpating a root canal to provide a properly dimensioned cavity while essentially maintaining the central axis of the canal. This step is important in order to enable complete filling of the canal without any voids and in a manner which prevents the entrapment of noxious tissue in the canal as the canal is being filled.

In cleaning and enlarging the root canal, instruments called files or reamers are used. Commonly, both files and reamers have flutes which spiral along a portion of the instrument length, and whether the instrument is a file or a reamer is determined by the pitch of the flutes. A greater pitch enables the instrument to cut better in a rotary mode, hence a reamer, and a lesser pitch enables the instrument to cut better in the reciprocating mode, hence a file. During a cleaning and shaping operation performed with such a file or reamer, the instrument is normally rotated and moved into and out of the root canal along the longitudinal axis of the instrument.

A widely used type of file or reamer is known by the designation "K-file" or "K-reamer". These instruments are made from a tapered rod which may be triangular or square in cross-section. The instruments are fabricated from the rods by twisting the rod to form a generally helical flute along the working portion of the rod, or the helical flute may be machined into the shaft.

The K-type instruments have several disadvantages. First, the instruments have a tendency to transport the central axis of a curved canal as the instrument cuts, mostly where the greatest pressure is exerted against the wall of the canal. Second, as the instruments are continuously rotated, the blades can become locked into the canal causing the instrument to break.

Finally, when modifications are made on conventional files and reamers to limit the tendency of the instrument to act as a screw or to diminish canal transportation, the tissue removal efficiency is generally sacrificed, particularly when a substantially non-circular canal is encountered as in a "fin" or "anastomosis."

It is therefore an object of the invention to provide an improved endodontic dental instrument.

Another object of the invention is to provide an endodontic dental instrument which enables improved removal efficiency of material from a root canal.

A further object of the invention is to provide an endodontic dental instrument having high tissue removal efficiency for non circular and/or curved root canals in addition to generally straight, circular canals.

SUMMARY OF THE INVENTION

With regard to the above and other objects, the present invention is directed to an endodontic dental instrument for use in extirpating and enlarging a root canal. The instrument comprises an elongate shank having a drive end and a tip end and preferably tapers toward the tip end. A working portion extends along at least a portion of the shank between the drive end and the tip end. The working portion includes at least one helical radial land spaced from a helical blade edge by a helical flute. Preferably, the land and blade edge spiral the working portion at substantially the same pitch. In one embodiment, the working portion is asymmetrical, that is, it includes a combination of a helical bearing surface defined by a helical radial land and a helical blade edge generally juxtaposed with respect to the land and spaced therefrom by at least a pair of helical flutes located on opposite sides of the blade edge between the edge and the land.

By the claimed structure, the helical blade edge is urged into cutting engagement to a greater degree than the helical land portion of the file as the file is rotated in the canal. However, the blade edge is forced to cut more equally on the inside and outside of the canal curvatures than conventional symmetric instruments which have a tendency to cut primarily on only one side of a canal curvature due to the forces imposed on the canal wall by the instrument when it is in bending flexure.

The working portion therefore may include at least one helical radial land having helical flank edges which define a bearing surface therebetween, and at least one helical blade-like edge which, when viewed in cross-section, is generally juxtaposed with the land.

In a further embodiment, the working portion may have two spaced apart helical radial lands and a blade edge, all of which are spaced apart about 120° viewed in cross-section, and the lands and blade edge have substantially the same pitch. Helical flutes subtend the lands and blade edge.

In yet another embodiment, the working portion has three spaced-apart helical radial lands when viewed in cross-section, each having helical flank edges so as to define a helical bearing surface on each land, and a helical blade edge located between two of the lands.

In another embodiment, the working portion includes one or more spaced-apart helical blade edges terminating inwardly of the periphery of the working portion, when viewed in cross-section, and a helical radial land disposed between the blade edges. In a further embodiment the working portion includes helical radial lands that intermittently narrow into blade edges and where both the lands and blade edges project essentially the same distance from the central axis of the instrument.

Each embodiment of the invention is therefore characterized by a working portion having one or more helical radial lands adjacent one or more helical blade-like edges which may advance along the shank toward the tip at the same or a different pitch relative to the land or lands. The land or lands may be continuous end-to-end or it or they may be discontinuous, such as being interrupted by an additional helical flute advancing toward the tip end at a substantially different pitch, intersections of the additional flute with the land or lands defining helically spaced apart sections of a blade-like edge. Therefore, the blade-like cutting edge or blade edges may also be continuous or discontinuous and may be adjacent the land or lands by virtue of having been defined by one or more land/flute intersections along the working portion.

The helical radial land or lands in the embodiments of the invention in combination with one or more helical blade edges enable improved cutting efficiency and control, which is particularly evident in working curved canals and non-circular curved canals, providing more uniform and complete material removal. The helical radial land bears against the canal surface to limit lateral transportation of the working portion relative to the original canal axis, while causing the working portion to self-advance into fin or anastomasi areas of the canal missed by conventional instruments.

BRIEF DESCRIPTION OF THE DRAWINGS

The above and other features of the invention will now be further described in the following detailed description of various embodiments in conjunction with the accompanying drawings in which:

FIG. 1 is an elevational view of an endodontic dental instrument according to one embodiment of the invention;

FIG. 2 is a cross-sectional view of the endodontic dental instrument of FIG. 1 taken along line 2—2 thereof;

FIG. 3 is a partial longitudinal view in section of the dental instrument of FIG. 1 taken along line 3—3 thereof;

FIG. 4 is an elevational view of an endodontic dental instrument according to another embodiment of the invention;

FIG. 5 is a cross-sectional view of instrument of FIG. 4 taken along the line 5—5 of FIG. 4 thereof;

FIG. 6 is a partial sectional view of the instrument of FIG. 4 taken along line 6—6 thereof;

FIG. 7 is an elevational view of an endodontic dental instrument according to still another embodiment of the invention;

FIG. 8 is a cross-sectional view taken along the line 8—8 of FIG. 7;

FIG. 9 is a partial sectional view of the instrument of FIG. 7 taken along line 7—7 thereof;

DETAILED DESCRIPTION OF THE PREFERRED EMBODIMENTS

Figure 10:
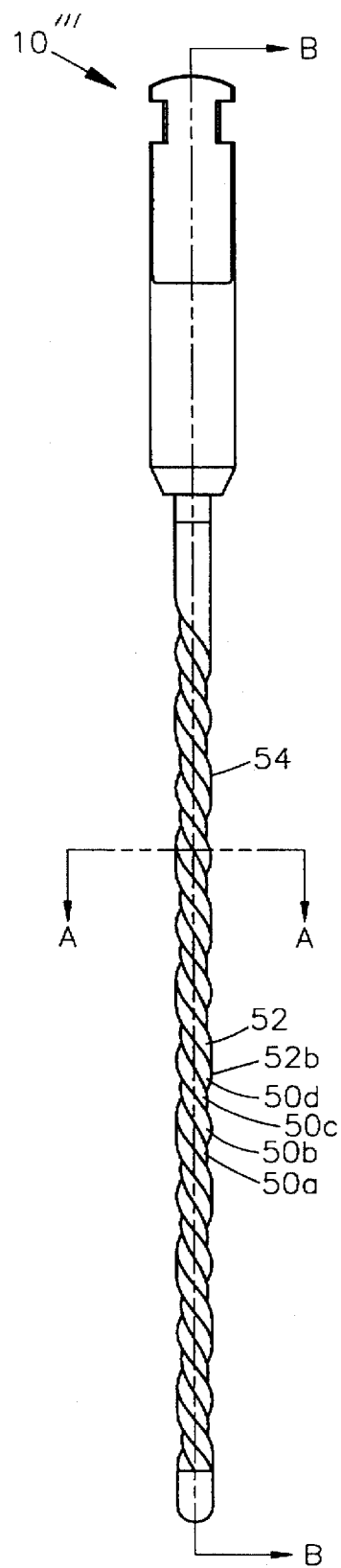
FIG. 10 is an elevational view of endodontic dental instrument according to yet another embodiment of the invention.

The figures illustrate dental instruments having various working portion configurations within the scope of the appended claims which may be used as a file or reamer for removing material from the root canal of a tooth. Referring first to FIGS. 1—3, there is shown a file generally denoted as 10 having a head portion 12 at its proximal end and a shank-like working portion 14, which is preferably tapered, extending along at least a portion of the length of the file 10 and a substantially cylindrical dome-end pilot 16 at the distal end. The cylindrical pilot 16 is well known and more fully described in U.S. Pat. No. 4,332,561 to McSpadden, incorporated herein by reference as if fully set forth. The pilot 16 is preferred, but is not required.

The head or driving end 12 of the file 10 contains a fitting portion 13 formed in the upper portion of the head for mating with a chuck of a dental handpiece (not shown). Alternately, or in addition to the fitting 13, the head 12 may include a knurled or otherwise treated surface to facilitate hand manipulation of the file 10.

The working portion 14 is comprised of one or more blade-like helical cutting edges 22 and one or more helical radial lands 18 (one each in the embodiment of FIG. 1). In the illustrated embodiment, helical flutes 20a and 20b subtend blade edge 22, and land 18. That is, flute 20a is spaced about 90° from flute 20b so as to define helical radial land 18 opposite the blade edge 22 which lies between flutes 20a and 20b at the periphery of the working portion 14 so that the flutes 20a and 20b subtend each side of the land 18 and the edge 22.

As shown in FIG. 2, blade edge 22 is generally opposite a bearing surface 19 of radial land 18. A used herein, A "radial" in connection with the lands means that the bearing surface 19 of the land 18 is curvilinear as opposed to flat, when viewed in cross-section. The walls of flutes 20a and 20b intersect the periphery of the working portion 14 in regions denoted by the letters A, B and C immediately adjacent the shank periphery at an angle of about 90 degrees to tangent to form what is commonly referred to as a zero or neutral rake angle from the perspective of the surfaces of the flutes 20a and 20b. For purposes of this invention, the rake angle can be neutral, positive or negative but is preferably about neutral.

It will be appreciated that radial land 18 presents bearing surface 19 between land flank edges 18a and 18b (FIGS. 2 and 3) so that when rotated in a canal in a counterclockwise direction, only flank edge 18b cuts while surface 19 bears against the canal wall. Land flank edges 18a and 18b are located at the periphery of the working portion 14 on opposing sides of the bearing surface 19 of radial land 18. Blade edge 22 also lies at the periphery of the working portion between flutes 20a and 20b, and is about 180° from the bearing surface 19.

FIGS. 4-6 illustrate another embodiment of an endodontic dental instrument 10' according to the invention. In this embodiment, three flutes subtend a radial land and blade-like cutting edges in a working portion 25. As shown in FIG. 5, a first flute 26a and a third flute 26c are on opposite sides of helical radial land 28. Flutes 26a and 26b are on opposite sides of a blade edge 30a and flutes 26b and 26c are on opposite sides of a blade edge 30b. Flute 26b is generally opposite a bearing surface 32 of land 28.

The walls of flutes 26a, 26b and 26c intersect the periphery of the working portion 25 immediately adjacent the shank periphery at an angle of about 90 degrees. Blade edges 30a and 30b are nominally about 90° apart.

Land flank edges 28a and 28b lie on the periphery of the working portion 25 on opposing sides of the bearing surface 32 of land 28. Helical blade-like cutting edges 30a and 30b and land flank edges 28a and 28b are therefore subtended by flutes 26a, 26b and 26c and lie at the periphery of the working portion 25. In counterclockwise rotation, only land flank edge 28a provides a cutting edge.

Thus, according to this embodiment, there are at least three helical flutes with a helical radial land between two of the flutes and blade-like cutting edges between two pairs of the flutes with the blade edges spaced apart about 90° and each spaced about 130° from an adjacent land flank edge, such that in cross section there is one land and three flutes, providing another embodiment of an asymmetrical working portion 25 according to the invention.

Yet another embodiment of an endodontic instrument 10" according to the invention is illustrated in FIGS. 7-9. In this embodiment, two continuous helical radial lands 36A and 36B are formed in and along a working portion 38 of the dental instrument 10". As shown in FIG. 8, helical land 36A originates nominally about 120° from helical land 36B such that helical lands 36A and 36B are subtended by a helical flute 40b. There are two helical flutes 40a and 40c subtending each side of a blade-like cutting edge 42 and lands 36B and 36A, respectively.

Flutes 40c and 40b are on opposite sides of a bearing surface 44 of land 36A. Flutes 40b and 40a are on opposite sides of bearing surface 46 of land 36B. The walls of flutes 40a, 40b and 40c intersect the periphery of the working portion 38 immediately adjacent the shank periphery at an angle of about 90 degrees to tangent of the shank periphery.

FIG. 9 illustrates land flank edges 36a and 36b on the shoulders of land 36A and land flank edges 36c and 36d on the shoulders of land 36B. During clockwise rotation of the instrument, flank edges 36b and 36c provide cutting edges.

Blade edge 42 between helical flutes 40a and 40c is also illustrated. All of the edges 42, 36a, 36b, 36c, and 36d are located on the periphery of the working portion 38. According to this embodiment, there are thus provided three helical flutes separated by two lands and a blade-like cutting edge with the lands spaced apart nominally about 120° and the blade edge spaced about 120° from the lands between the lands, providing an asymmetrical working portion according to the invention.

Figure 11:
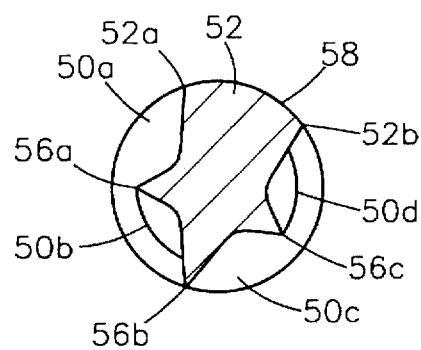
FIG. 11 is a cross-sectional view taken along the line 11—11 of FIG. 10.
Figure 12:
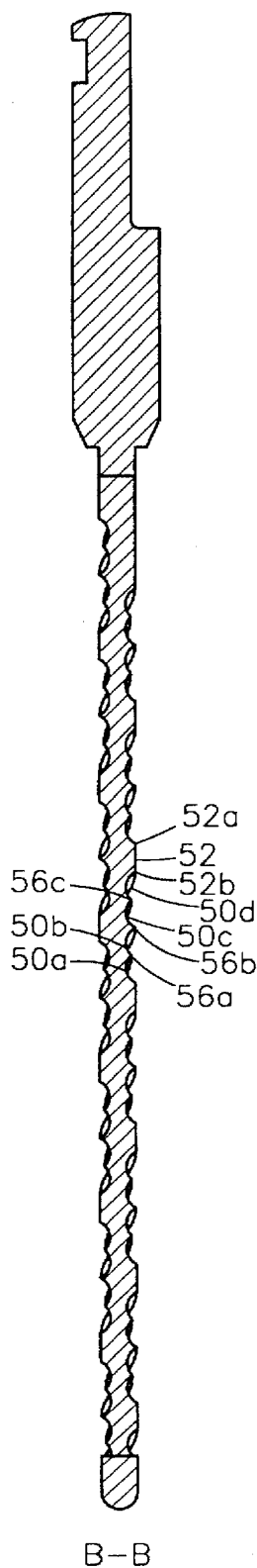
FIG. 12 is a partial sectional view of the instrument of FIG. 10 taken along line 12—12 thereof.

FIGS. 10–12 illustrate still another endodontic instrument 10''' according to the invention. In this instrument, there are four helical flutes 50a, 50b, 50c and 50d and one helical radial land 52 between each set of four helical flutes formed in and along an asymmetrical working portion 54 of the dental instrument. The helical flutes subtend helical blade-like cutting edges 56a, 56b and 56c and land flank edges 52a and 52b of land 52. In counter-clockwise rotation of the instrument, flank edge 52b is a cutting edge.

Blade edge 56b is at the periphery of the working portion 51 and opposite helical radial land 52. In this embodiment, blade edges 56a and 56c do not extend to the periphery of the working portion, but terminate at a point which is spaced inwardly of the circumference of the periphery defined by bearing surface 58 and blade edge 56b.

The relationship of blade edges 56a, 56b and 56c is best seen in FIG. 11. Blade edge 56a is between flutes 50a and 50b, blade edge 56b is between flutes 50b and 50c and blade edge 56c is between flutes 50c and 50d. Flutes 50a and 50d each are on opposite sides of a bearing surface 58 of land 52. One side of the wall of each of flutes 50a, 50b, 50c and 50d intersects the periphery of the working portion 54 immediately adjacent the shank periphery at an angle of about 90 degrees to tangent of the shank periphery. The other sides of the walls of flutes 50a, 50b, 50c and 50d terminate at blade edges 56a and 56c spaced inwardly of the circumference of the periphery of the working portion 54 as defined by bearing surface 58 and blade edge 56b.

Thus, according to this embodiment, the instrument includes four helical flutes with one helical radial land, two of the flutes merging to provide a blade-like cutting edge adjacent the periphery spaced about 180° from the land, and opposed pairs of intersecting flutes merging to provide blade-like cutting edges also about 180° apart from one another spaced inwardly of the periphery and shifted nominally about 90° relative to the land, the arrangement providing an asymmetrical working portion according the invention.

Figure 13:
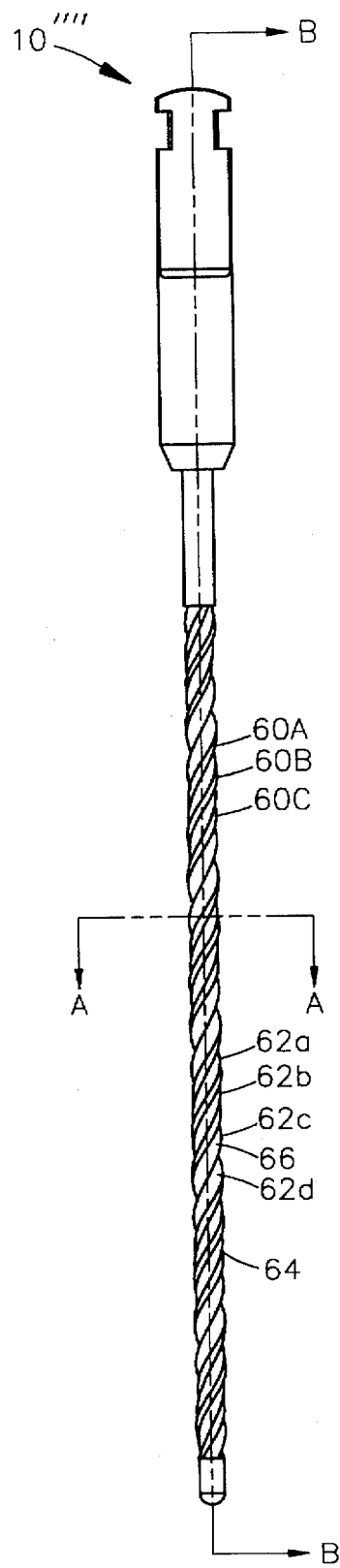
FIG. 13 is an elevational view of an endodontic dental instrument according to still another embodiment of invention.
Figure 14:
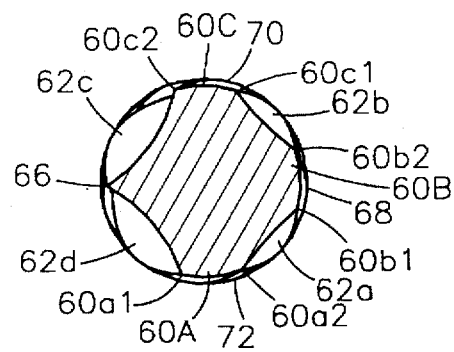
FIG. 14 is a cross-sectional view taken along the line 14—14 of FIG. 13.
Figure 15:
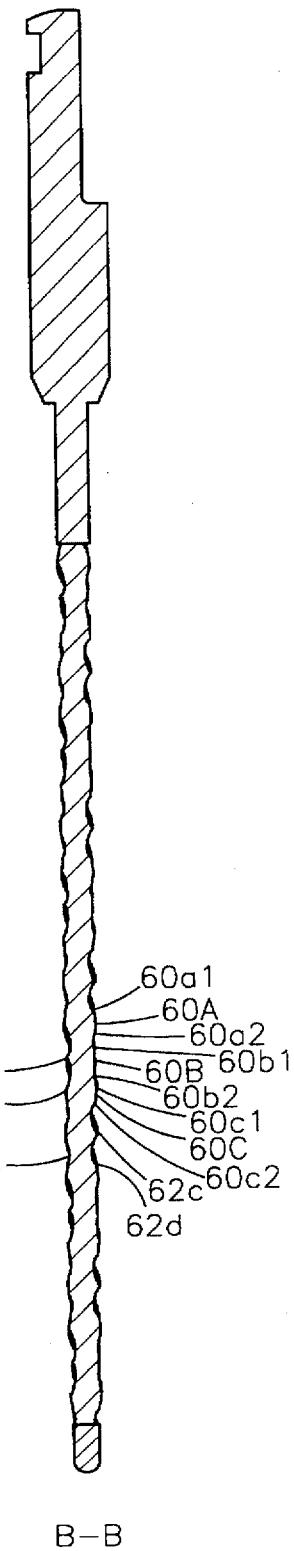
FIG. 15 is a partial sectional view of the instrument of FIG. 13 taken along line 15—15 thereof.

A further endodontic instrument 10''' according to the invention is illustrated in FIGS. 13–15. In this instrument, three helical radial lands 60A, 60B and 60C and four helical flutes 62a, 62b, 62c and 62d are provided in and along the working portion 64. The helical flutes 62c and 62d subtend each side of blade-like cutting edge 66 and lands 60C and 60A, the edge 66 lying at the periphery of the working portion 64 and opposite helical land bearing surface 68 of helical land 60B. All of the helical lands and the blade edges in this embodiment extend to the periphery of the working portion 64.

The relationship of blade-like cutting edge 66 and lands 60A, 60B and 60C is best seen in FIG. 14. As shown, blade edge 66 is between flutes 62c and 62d whereas bearing surface 68 of helical land 60B is between flutes 62a and 62b spaced from edge 66 about 180°. Bearing surface 70 of helical land 60C is between flutes 62b and 62c, and bearing surface 72 of helical land 60A is between flutes 62d and 62a. The walls of flutes 62a, 62b, and 62c directed toward lands 60A, 60B, and 60C intersect the periphery of working portion 14 immediately adjacent the shank periphery at an angle substantially less than about 90 degrees to tangent of the shank periphery. The walls of flutes 62c and 62d directed toward edge 66 intersect the shank periphery at an angle nominally of about 90°.

As shown in FIG. 15, flank edges $60a_1$, $60a_2$, $60b_1$, $60b_2$, $60c_1$, and $60c_2$ are on the shoulders of lands 60A, 60B and 60C, respectively. All of these land flank edges are located on the periphery of the working portion 64. In clockwise rotation of the instrument, flank edges $60a_2$, $60b_2$, and $60c_2$ provide cutting edges According to this embodiment, there are three helical radial lands and a blade-like edge all spaced-apart nominally about 90° and four helical flutes separating the lands and the blade edge to provide a working portion according to the invention.

The endodontic instruments of the invention provide improved removal of material in the root canal of a tooth due to the combination of helical cutting blades and bearing surfaces along the working portion. Accordingly, the endodontic instruments of the invention have been found to have improved side cutting capability and an inherent propensity to work into canal areas that are noncircular so as to remove material from anastomosi previously untouched or insufficiently worked by conventional instruments, as well as move evenly working curvilinear canals.

The endodontic instruments of the invention may be used by manipulating the file manually in a rotating/reciprocating action, or the file or reamer may be manipulated by attaching the instrument to a motorized device for effecting the removal of material from the root canal. As depicted in the foregoing illustrations the working portion extends a substantial distance along the length of the instrument and may possess a generally tapered configuration as a path is traced from the drive end of the working portion to the tip end. The diameter of the working portion may increase from about 0.01 to about 0.07 mm, preferably about 0.02 mm, for each millimeter up the working portion from the tip end to the drive end. The entire working portion of the shank may be about 20 to 30 mm, but longer or shorter working portions may be used. The diameter of the working portion adjacent the tip end may range from about 0.08 to about 1.9 millimeters.

The rake angles of the blade edges may be positive, negative, or neutral, but are preferably about neutral with respect to the periphery of the working portion. In order to make the instruments having the desired rake angles, the instruments may be ground from a straight or tapered rod, twisted and/or drawn to a taper with or without grinding.

The endodontic instruments of the invention are preferably made form surgical stainless steel, however, they can also be made from composite materials such as nickel titanium or other "exotic" alloys, and the like. The preferred material for the instruments of the invention is nickel titanium or titanium 13—13. Those of ordinary skill will recognize that techniques for making conventional instruments may generally be applied to the manufacture of instruments according to the invention and with various known or later-developed materials. Suitable grinding techniques which may be used are described in metallurgical texts for grinding metals. For example, it is known that certain grinding wheels or bits for making instruments out of one material may not be effective for other or different materials. While a grinding surface made of course grit and rotating at a relatively high speed may be suitable for grinding stainless steel or a hard metal shaft, a nickel-titanium shaft may require a finer grit grinding surface rotating at a relatively slower speed in order to effectively abrade the shaft to form the necessary edges and lands.

The foregoing detailed description is given for understanding of the invention and to illustrate its various features and known advantages, but no unnecessary limitations are to be understood therefrom. Modifications of the various illustrated embodiments and, indeed, the fashioning of other or even improved embodiments, some of which may be obvious to those skilled in the art upon reading the disclosure, may be made without departing from the spirit and scope of the invention as defined by the appended claims.

What is claimed is:

1. An endodontic dental instrument for extirpating and enlarging a wall of a root canal which comprises an elongate shank having a drive end and a tip end with a working portion defined along at least a portion of the length of the shank between the tip end and the drive end, the working portion including a helical radial land and a helical blade edge having substantially no land with a first helical flute disposed between said land and said helical blade edge on one side of said blade edge and a second helical flute disposed between said helical blade edge and said land on the other side of said blade edge.

2. The instrument of claim 1 wherein the shank tapers from a point adjacent the drive end to a point adjacent the tip end.

3. The instrument of claim 1 wherein the land defines a curvilinear bearing surface which provides, with respect to at least one direction of rotation of the shank about its longitudinal axis, a leading helical blade edge on the land and a trailing helical edge with the bearing surface therebetween, the blade edge being ahead of the leading edge and spaced therefrom by said first flute.

4. The instrument of claim 3 wherein said shank is tapered from a point adjacent said drive end to a point adjacent said tip end.

5. The Instrument of claim 1 wherein the first and second helical flutes span completely between said blade edge and said land.

6. The instrument of claim 1 wherein said second helical flute subtends said helical radial land and said helical blade edge on one side of said blade edge and said first helical flute subtends said helical land and said helical blade edge on an opposing side of said blade edge.

7. The instrument of claim 1 further comprising a second helical blade edge spaced from said blade edge by said second helical flute and a third helical flute disposed between said second helical blade edge and said radial land.

8. The instrument of claim 1 further comprising a second helical radial land spaced from said land by a third helical flute and a fourth helical flute disposed between said second helical land and said helical blade edge.

9. The instrument of claim 1 further comprising a second helical blade edge spaced from said blade edge by a third helical flute and a fourth helical flute disposed between said second blade edge and said radial land.

10. The instrument of claim 9 further comprising a third helical blade edge spaced from said second blade edge by a fifth helical flute wherein said fourth helical flute separates said second helical blade edge from said third helical blade edge and said fifth helical flute separates said third helical blade edge and said helical radial land.

11. The instrument of claim 1 wherein the pitch of any of one of said blade edges is different form the pitch of any one of said radial lands.

12. The instrument of claim 1 wherein a second helical flute is disposed at a pitch different from that of said first helical flute so as to intersect both said helical land and said helical flute at successive spaced apart intersections to define by said intersections a helically disposed, spaced apart series of segments of a generally helically arranged blade edge having at least a radial component.

13. An endodontic dental instrument for extirpating and enlarging a wall of a root canal which comprises an elongate shank having a drive end and a tip end with a working portion defined along at least a portion of the length of the shank between the tip end and the drive end, the working portion including a helical radial land and a helical blade edge with a first helical flute disposed between said land and said helical blade edge on one side of said blade edge and a second helical flute disposed between said helical blade edge and said land on the other side of said blade edge and further comprising a second helical blade edge spaced from said blade edge by a third helical flute and a fourth helical flute disposed between said second blade edge and said radial land wherein at least one of said helical blade edges terminates radially inwardly of an adjacent blade edge.

14. The instrument of claim 13 wherein the pitch of any of one of said blade edges is different form the pitch of any one of said radial lands.

15. The instrument of claim 13 wherein said shank is tapered from a point adjacent said drive end to a point adjacent said tip end.

16. An endodontic dental instrument for extirpating and enlarging a wall of a root canal which comprises an elongate shank having a drive end and a tip end with a working portion defined along at least a portion of the length of the shank between the tip end and the drive end, the working portion including a helical radial land and a helical blade edge with a first helical flute disposed between said land and said helical blade edge on one side of said blade edge and a second helical flute disposed between said helical blade edge and said land on the other side of said blade edge and a second helical blade edge spaced from said blade edge by a third helical flute and a fourth helical flute disposed between said second blade edge and said radial land and a third helical blade edge spaced from said second blade edge by a fifth helical flute wherein said fourth helical flute separates said second helical blade edge from said third helical blade edge and said fifth helical flute separates said third helical blade edge and said helical radial land wherein at least one of said helical blade edges terminates radially inwardly of an adjacent blade edge.

17. The instrument of claim 16 wherein the pitch of any of one of said blade edges is different form the pitch of any one of said radial lands.

18. The instrument of claim 17 wherein said shank is tapered from a point adjacent said drive end to a point adjacent said tip end.

* * * * *